United States Patent [19]

Zimmermann

[11] Patent Number: 4,577,303
[45] Date of Patent: Mar. 18, 1986

[54] TEST EQUIPMENT FOR PHONO PICKUP NEEDLES

[76] Inventor: Heinrich Zimmermann, Joh.-Seb.-Bach-Str. 14, D-7742 St. Georgen, Fed. Rep. of Germany

[21] Appl. No.: 622,799

[22] Filed: Jun. 21, 1984

[30] Foreign Application Priority Data

Jun. 21, 1983 [DE] Fed. Rep. of Germany ....... 3322230

[51] Int. Cl.$^4$ .......................... G11B 3/00; H04N 5/76
[52] U.S. Cl. ........................................ 369/55; 369/53
[58] Field of Search .......................... 369/53, 55; 73/9

[56] References Cited

U.S. PATENT DOCUMENTS

| | | | |
|---|---|---|---|
| 2,091,022 | 8/1937 | Stuart | 73/9 |
| 2,740,296 | 4/1956 | Andres | 369/55 |
| 3,328,037 | 6/1967 | Lehmann et al. | 369/53 |
| 3,481,609 | 12/1969 | Lukens | 369/53 |
| 4,165,078 | 8/1979 | Kuehn | 369/55 |
| 4,375,095 | 2/1983 | Keizer | 369/55 |

FOREIGN PATENT DOCUMENTS

| | | | |
|---|---|---|---|
| 468067 | 11/1928 | Fed. Rep. of Germany | 369/55 |
| 864755 | 7/1949 | Fed. Rep. of Germany | 369/55 |

Primary Examiner—Steven L. Stephan
Attorney, Agent, or Firm—Horst M. Kasper

[57] ABSTRACT

Test equipment is provided for determining the size or the degree of wear of a phono pickup needle. The static friction which is experienced by a motion of the stylus in the groove of a record is measured. The test equipment employs components of a record player and includes a turntable capable of being turned manually. A base part is positioned on the turntable. An axis is disposed at the base part. A carrying part is supported by the base part and is rotatable about the axis such that the carrying part moves about in a plane parallel to the base part on the turntable. A test support area is made of a material corresponding to a phonograph record. The test support area is provided with grooves and rests on the carrying part such that the grooves correspond in their position to the grooves of a record and such that the stylus engages a groove. Elastic coupling means is provided between the carrying part and the base part. The restoring force of the coupling means increases with increasing relative turning of the base part with respect to the carrying part. Display means indicates the relative turning of the base part with respect to the carrying part.

18 Claims, 2 Drawing Figures

TEST EQUIPMENT FOR PHONO PICKUP NEEDLES

BACKGROUND OF THE INVENTION

1. Field of the Invention

The present invention relates to a test apparatus for phonograph pickup needles and styli for determining the amount of wear of the scanning point of the styli.

2. Brief Description of the Background of the Invention Including Prior Art

Conventional test equipment of the kind set forth above usually comprises essentially a microscope, a special support provision for a reproducing needle, and an illumination provision. The magnification has to be such that the length of the ground-off surface of the point of the needle of for examaple 5 to 8 micrometers can be easily recognized, since an elliptically ground needle follows the flanks of the grooves because of the short wavelengths of about 15 micrometer for example with a radius of only 5 to 8 micrometer.

Therefore, such test equipment is expensive and not suitable for the general consumer. Because of the relatively high price frequently insufficient microscopes, in particular with respect to the magnification, are employed and thus the determination of the degree of wear becomes indefinite. In addition to the existing technical problems there is further present in many cases a lack of confidence between the customer and the shop or, respectively, the seller of the needle.

In view of this, simple provisions for the general consumer to determine the wear of a needle are already known. These provisions determine the wear in an indirect way by measuring the playing time (German Patent Application Laid Out DE-AS No. 1,091,359 and British Patent Specification No. 2,045,994). In fact, these provisions are substantially cheaper and can also be manipulated easily by the general consumer, but they are associated with the disadvantage that they lead to very inaccurate results. For example, the size of the rounding radius can be taken summarily from a table for correction purposes of the playing time in case of sapphire or diamond, but this is no longer in general possible because of the considerable hardness differences, which can for example amount to a ratio of 1:5 in the case of diamond depending on the disposition of the crystal axes. The same holds true for differing wear hardnesses of phonorecords. In addition, the determination of the actual scanning path length, over which the needle passes, proves to be difficult (German Patent Application Laid Out Nos. 1,200,009 and 1,211,416).

SUMMARY OF THE INVENTION

1. Purposes of the Invention

It is an object of the present invention to provide for a substantially more accurate way of determining the degree of wear of a stylus.

It is another object of the present invention to determine the degree of wear of a stylus by a method which largely approximates the use conditions of the stylus.

It is a further object of the present invention to provide a method of stylus wear determination, which can be handled by the general consumer.

These and other objects and advantages of the present invention will become evident from the description which follows.

2. Brief Description of the Invention

The present invention provides test equipment for reproducing styli for records to determine the amount of wear of the scanning tip of a stylus. The equipment employs components of a record player and comprises a turntable capable of being turned manually. A reproducing stylus used for a scanning of records is tested. A pickup supports the reproducing stylus. A base part is positioned on the turntable. An axis is disposed at the base part. A carrying part is supported by the base part and rotatable about the axis such that the carrying part is movable about in a plane parallel to the base part on the turntable. A test support area is made of a material corresponding to a record, which test support area is provided with grooves and which test support area rests on the carrying part such that the grooves correspond in their position to the grooves of a record and the stylus engages a groove. Elastic coupling means is provided between the carrying part and the base part, where the restoring force of the coupling means increases with increasing relative turning of the base part with respect to the carrying part. A display means indicates the relative turning of the base part with respect to the carrying part.

The coupling means can comprise a spring to provide a restoring force. Alternatively, the coupling means can comprise a magnetic interaction element generating a force upon turning of the base, or the gravitational force can be employed as a restoring force.

The axis can be disposed at a distance from the grooves and, respectively, the stylus engages a groove such that the base part is movable in a horizontal plane relative to the carrying part. The base part can include a support arm directed upwardly. The axis can be provided as a horizontal axis and is disposed near the upper end of the support arm. The carrying part can include a pendulum tiltably hanging on the horizontal axis and a carrying plate disposed at the lower end of the pendulum for supporting the test support area. The base part can be placed on the turntable such that the grooves of the test support area correpsond to the position of the grooves of a record placed on a turntable.

The turntable can alternatively be provided with a centering axis. The base part can be provided with a bore for placing it onto the centering axis of the turntable. A carrying part can be disposed like a shell and can be rotatable around the axis disposed at the base part. The axis disposed at the base part can be connected to the base part and disposed coaxially with respect to the centering axis of the turntable. The test support area can provided as a disk having a bore at the center corresponding to the shell like carrying part. The lower part of the test support area can be provided by a flange for supporting the test support area.

The coupling means between base part and carrying part can be provided as a helical spring disposed concentrically to the axis disposed at the base part. The display means can comprise a mask disposed at the upper edge of the carrying part and located concentrically to the rotation axis of the carrying part and a scale can be attached to the base part and be disposed oppositely to said mask.

The shell like carrying part can have a diameter corresponding to the center bore of a commerical record and a test support area including a commercial record. The center bore can be about 38 millimeter (1.5 inch). The test support area can be secured with an elastic ring to the carrying part.

There is also provided a method for testing reproducing styli for records to determine the amount of wear of the scanning tip of a stylus, where components of a record player are employed. A reproducing stylus to be tested and used for a scanning of records can be placed at a pickup. A base part having an axis can be positioned on a turntable. A carrying part can be supported by the base part, where the carrying part is rotatable about the axis such that the carrying part is movable about in a plane parallel to the base part on the turntable. The carrying part and the base part can be coupled elastically such that the restoring force of a coupling means increases with increasing relative turning of the base part with respect to the carrying part. A test support area made of a material corresponding to a record can be placed onto the carrying part, and the test support area is provided with grooves and rests on the carrying part such that the grooves correspond in their position to the grooves of a record and, the stylus engages a groove. Then the turntable can be turned. The relative turning of the base part with respect to the carrying part can be displayed.

The coupling means can comprise a spring to provide a restoring force, a magnetic interaction element for generating a force upon turning of the base and/or the gravitational force can be employed as a restoring force.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention.

DESCRIPTION OF INVENTION AND PREFERRED EMBODIMENT

Figure 1:
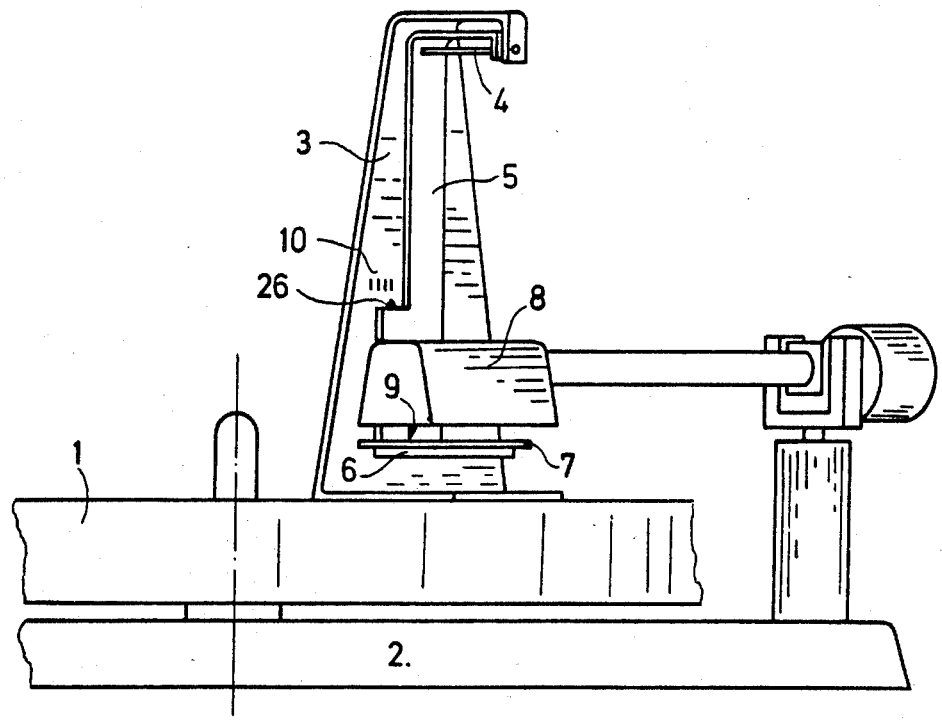
FIG. 1 is a schematic view of a first embodiment of the test equipment for phono pickup needles according to the present invention.

In accordance with the present invention there is provided a test apparatus for the scanning of phono records for determining the amount of wear of the scanning point tip of the needle. With increasing wear of the scanning tip of a stylus its sliding friction resistance against a motion from the rest position increases and the size of this sliding friction resistance is employed for determining the degree of wear. The change of the sliding friction resistance, which decreases with increasing wear, is a result of the increase in size of the area of the needle ground off and the decreased pressing and squeezing force, since in case of an increased support surface the needle can penetrate into the phonograph record surface only to a lesser degree. The sliding friction resistance is composed of pressing force and friction force. The friction force has no influence on the change of the sliding friction resistance, since the friction coefficient is independent of the size of the contact area and of the contacting pressure. It is known that the frictional resistance is smaller during motion as compared with the change from rest into motion. Of course this holds also for the sliding friction resistance of the needle. The resistance from the rest state into a moving state (static friction resistance) depends more strongly on the size of the wear area or on the penetration depth of the needle and it is employed for the determination of the degree of wear according to the present invention. For example, a new scanning needle with a tip rounding radius of 7 micrometer in the area of the groove flanks exhibits usually a static friction resistance of 7.2 mN under a contacting force of 15 mN. After about 400 hours of playing time, where a 25 micrometer large wear surface is generated, the static frictional resistance decreases to 2.5 mN. In case of a rounding radius of 17 micrometer and the same contacting force the static frictional resistance decreases from 5.25 mN to 2.7 mN after the same wear.

This shows not only how strongly the static friction force depends on the degree of wear of the needle, but also to which extent it depends on the rounding radius proper, that is in the state where the needle has not been used.

It results herefrom that the measurement of the static friction force is suitable not only for the determination of the degree of wear of the needle, but also for determining the size of the rounding radius in the new state. This can be of importance in the production of the needle, since such a determination of the radius at a high accuracy is simpler as compared to a microscopic determination, since here the relative sizes of the radii can be displayed directly. In the following the same items in the two Figs. are designated with the same numerals.

A record player 2 is employed with a turntable 1, which can be rotated manually. A sound pickup 8 with a scanning stylus 9 for following the grooves of a record is mounted on the record player 2. A base part 3, 11 can be positioned on the turntable 1. A test support area 7, 17 comprises a material, which corresponds in its properties to phonograph records and which has its surface provided with grooves. The test support area 7, 17 is disposed on a carrying part 6, 13, 19 such that the sound grooves with respect to their position correspond to those of a phonograph record. The carrying part 6, 13, 19 is connected to the base part 3, 11 via an axis 4, 14. The axis 4, 14 is disposed at a distance from the sound grooves or, respectively, from the reproducing needle 9 placed in a groove such that the base part can be moved in a horizontal plane relative to the carrying part 6, 13, 19. A coupling means 21, 5 based on a spring, magnetic or gravitational force is installed between the carrying part 6, 13, 19 and the base part 3, 11. The coupling force of the coupling means 21, 5 increases with increasing amount of deviation from the mutual rest position of carrying part 6, 13, 19 and base part 3, 11. A display means 10, 26, 23, 16 is employed for indicating the mutual positional change of carrying part 6, 13, 19 relative to the base part 3, 11.

According to FIG. 1 the base part 3 can comprise an upwardly directed support arm. The coupling means 5 for the carrying part 6 can be provided as a pendulum, which is at its upper end tiltably hung at the upwardly directed support arm of the base part 3 via an axis 4. A carrying plate 6 can be positioned at the lower end of the pendulum and can support the test support area 7.

A support bracket provides the base part 3, at the upper end of which a pendulum 5 is tiltably disposed around an axis 4. The pendulum 5 comprises at its lower end a carrying plate 6, which serves as a support part for a test support area 7 provided by a piece of a phonograph record, onto which the the phonograph pickup 8 with its reproducing needle 9 can be placed.

The base part 3 is placed advantageously such onto the turntable 1 such that the sound groove of the test support area 7 assumes approximately the usual position. If the turntable 1 is moved slowly by hand in the usual sense of rotation direction, then the base part 3 is carried by the axis 4 of the pendulum. Since the test support area 7 is retained by the static friction force of the needle 9, the pendulum 5 tilts and generates a restoring torque generated by the gravitational force and the restoring force is directed such as to return the test support area 7 into its starting position. This occurs only if the torque has become so great that its tangential force at the test support area 7 has become greater than the static friction force of the needle 9. The size of this torque, which is reached when the the needle starts to slide, which is the maximum value, can be read at a marker 26 at a scale 10 of the base part 3 and it corresponds to a certain state of wear.

Figure 2:
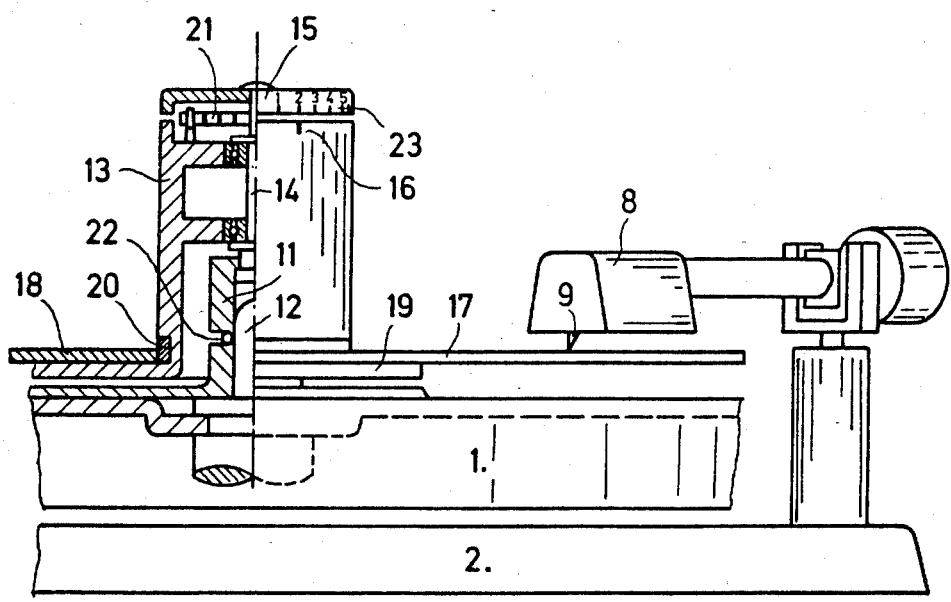
FIG. 2 is a schematic view of a second embodiment of the test equipment for phono pickup needles.

According to an alternative preferred embodiment shown in FIG. 2 a base part 11 is provided with a bore for placing it onto the centering axis 12 of the turntable 1. A carrying part 13, 19 is like a shell disposed rotatable around an axis 14. The axis 14 is connected to the base part 11 and is disposed coaxially with respect to the centering axis 12 of the turntable 1. The test support area 17 is formed as a disk, which is provided at its center with a bore of the diameter of the shell like carrying part 13. A flange 19 forms the lower part of the carrying part 13, 19 and serves to position the mentioned disk shaped test support area 17.

The coupling means between base part 11 and carrying part 13, 19 can comprise a helical spring 21 disposed concentrically with respect to the axis 14. The display means 16, 23 can comprise a mask 16, which is disposed at the upper edge of the carrying part 13 centered concentrically relative to its rotation axis 14, and a scale 23, which is attached at the base part such that it is positioned opposite to the mask 16. The diameter of the shell like carrying part 13 can be 38 millimeters and the test support area 17 can be a commercial phonograph record with a center bore of 38 millimeters.

The base part 11 can comprise a shell which can be attached with a frictional adhesion over the centering axis 12 of the turntable 1. A friction means 22 prevents a rotation of the shell versus the turntable 1. The base part 11 is extended upwardly by an axis 14 and a cap 15 is attached to the end of the axis 14. The cap 15 carries at its circumference a scale 23. A centering part 13 is rotatably disposed at the axis 13 of the base part 11. The centering part 13 has attached a flange 19, which serves as a supporting structure. A plate comprising sound grooves serves as a test support area 17 and rests on the flange 19. The plate is secured in its position with an elastic ring 20 disposed in the centering part 13. The centering part 13 is rotatably and elastically connected to the axis 14 of the base part 11 via a helical spring 21 and it carries at its upper edge a marker 16 positioned opposite to the scale 23 of the cap 15 of the base part 11.

If the turntable 1 is rotated by hand while the sound pickup needle rests on the test support area, then the static frictional resistance of the needle 9 prevents the plate 17 initially from rotating correspondingly. However, this tensions the spiral spring 21 and attempts to carry the spring along with increasing force, which succeeds however only when the force of the spiral spring 21 becomes larger than the static frictional resistance generated by the needle 9. The value thus reached can be read by the starting of the motion at this point in time of the marker 16 with the scale 23 or, respectively, of the stopping of a further change of the marker 16 versus the scale 23. This reading indicates the amount of wear.

It will be understood that each of the elements described above, or two or more together, may also find a useful application in other types of test system configurations and torque force measurement procedures differing from the types described above.

While the invention has been illustrated and described as embodied in the context of test equipment for phono pickup needles, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. Test equipment for reproducing styli for records to determine the amount of wear of the scanning tip of a stylus, which equipment employs components of a record player, comprising
   a turntable capable of being turned manually;
   a reproducing stylus to be tested used for a scanning of records;
   a pickup supporting the reproducing stylus;
   a base part to be positioned on the turntable;
   an axis disposed at the base part;
   a carrying part supported by the base part and rotatable about the axis such that the carrying part is movable about in a plane parallel to the base part on the turntable;
   a test support area made of a material corresponding to a record, which test support area is provided with grooves and which test support area rests on the carrying part such that the grooves correspond in their positon to the grooves of a record and where the stylus engages a groove;
   elastic coupling means between the carrying part and the base part, where the restoring force of the coupling means increases with increasing relative turning of the base part with respect to the carrying part; and
   display means indicating the relative turning of the base part with respect to the carrying part.

2. Test equipment for reproducing styli for records according to claim 1 wherein the coupling means comprises a spring to provide a restoring force.

3. Test equipment for reproducing styli for records according to claim 1 wherein the coupling means comprises employing the gravitational force as a restoring force.

4. Test euqipment for reproducing styli for records according to claim 1 wherein the axis is disposed at a distance from the grooves and, respectively, the stylus engages a groove such that the base part is movable in a horizontal plane relative to the carrying part.

5. Test equipment for reproducing styli for records according to claim 1 wherein the base part includes a support arm directed upwardly;

wherein the axis is provided as a horizontal axis and is disposed near the upper end of the support arm;

wherein the carrying part includes a pendulum tiltably hanging on the horizontal axis and a carrying plate disposed at the lower end of the pendulum for supporting the test support area; and wherein the base part is placed on the turntable such that the grooves of the test support area correspond to the position of the grooves of a record placed on a turntable.

6. Test equipment for reproducing styli for records according to claim 1 wherein the turntable is provided with a centering axis;

wherein the base part is provided with a bore for placing it onto the centering axis of the turntable;

wherein a carrying part is disposed like a shell and rotatable around the axis disposed at the base part;

wherein the axis disposed at the base part is connected to the base part and disposed coaxially with respect to the centering axis of the turntable;

wherein the test support area is provided as a disk having a bore at the center corresponding to the shell like carrying part; and wherein the lower part of the test support area is provided by a flange for supporting the test support area.

7. Test equipment for reproducing styli for records according to claim 6 wherein the coupling means between base part and carrying part is provided as a helical spring disposed concentrically to the axis disposed at the base part.

8. Test equipment for reproducing styli for records according to claim 6 wherein the display means comprises a mask disposed at the upper edge of the carrying part and located concentrically to the rotation axis of the carrying part and a scale attached to the base part disposed oppositely to said mask.

9. Test equipment for reproducing styli for records according to claim 6 wherein the shell like carrying part has a diameter corresponding to the center bore of a commercial record and a test support area including a commerical record.

10. Test equipment for reproducing styli for records according to claim 9 wherein the center bore is about 38 millimeters (1.5 inches).

11. Test equipment for reproducing styli for records according to claim 6 wherein the test support area is secured to the carrying part with an elastic ring.

12. A method for testing reproducing styli for records to determine the amount of wear of the scanning tip of a stylus, where components of a record player are employed, comprising placing a reproducing stylus to be tested used for a scanning of records at a pickup;

positioning a base part having an axis on a turntable;

supporting a carrying part by the base part, where the carrying part is rotatable about the axis such that the carrying part is movable about in a plane parallel to the base part on the turntable;

coupling elastically the carrying part and the base part where the restoring force of a coupling means increases with increasing relative turning of the base part with respect to the carrying part;

placing a test support area made of a material corresponding to a record onto the carrying part, which test support area is provided with grooves and which test support area rests on the carrying part such that the grooves correspond in their position to the grooves of a record and where the stylus engages a groove;

turning the turntable; and displaying the relative turning of the base part with respect to the carrying part.

13. A method for testing reproducing styli for records according to claim 12 wherein the coupling means comprises a spring to provide a restoring force.

14. A method for testing reproducing styli for records according to claim 12 wherein the coupling means comprises employing the gravitational force as a restoring force.

15. A method for testing reproducing styli for records according to claim 12 wherein the axis is disposed at a distance from the grooves and, respectively, the stylus engages a groove such that the base part is movable in a horizontal plane relative to the carrying part.

16. A method for testing reproducing styli for records according to claim 12 wherein the base part includes a support arm directed upwardly;

wherein the axis is provided as a horizontal axis and is disposed near the upper end of the support arm;

wherein the carrying part includes a pendulum tiltably hanging on the horizontal axis and a carrying plate disposed at the lower end of the pendulum for supporting the test support area; and wherein the base part is placed on the turntable such that the grooves of the test support area correspond to the position of the grooves of a record placed on a turntable.

17. A method for testing reproducing styli for records according to claim 12 wherein the turntable is provided with a centering axis;

wherein the base part is provided with a bore for placing it onto the centering axis of the turntable;

wherein a carrying part is disposed like a shell and rotatable around the axis disposed at the base part;

wherein the axis disposed at the base part is connected to the base part and disposed coaxially with respect to the centering axis of the turntable;

wherein the test support area is provided as a disk having a bore at the center corresponding to the shell like carrying part; and wherein the lower part of the test support area is provided by a flange for supporting the test support area.

18. A method for testing reproducing styli for records according to claim 17 wherein the coupling means between base part and carrying part is provided as a helical spring disposed concentrically to the axis disposed at the base part;

wherein the display means comprises a mask disposed at the upper edge of the carrying part and located concentrically to the rotation axis of the carrying part and a scale attached to the base part disposed oppositely to said mask.

* * * * *